United States Patent
Ellingson (10) Patent No.: US 10,524,686 B2
(45) Date of Patent: Jan. 7, 2020

(54) DIFFUSION REPRODUCIBILITY EVALUATION AND MEASUREMENT (DREAM)-MRI IMAGING METHODS

(71) Applicant: THE REGENTS OF THE UNIVERSITY OF CALIFORNIA, Oakland, CA (US)

(72) Inventor: Benjamin M. Ellingson, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 746 days.

(21) Appl. No.: 14/956,149

(22) Filed: Dec. 1, 2015

(65) Prior Publication Data

US 2016/0157746 A1    Jun. 9, 2016

Related U.S. Application Data

(60) Provisional application No. 62/085,715, filed on Dec. 1, 2014.

(51) Int. Cl.
*A61B 5/055* (2006.01)
*A61B 5/00* (2006.01)
(Continued)

(52) U.S. Cl.
CPC .......... *A61B 5/055* (2013.01); *A61B 5/7207* (2013.01); *G01R 33/56341* (2013.01); *G01R 33/561* (2013.01); *G01R 33/56518* (2013.01)

(58) Field of Classification Search
CPC .............. A61B 5/055; A61B 5/7207; G01R 33/56341; G01R 33/56509; G01R 33/4824; G01R 33/561; G01R 33/56518
(Continued)

(56) References Cited

U.S. PATENT DOCUMENTS

| 8,044,662 B2 * | 10/2011 | Fransson | ................. | G01N 24/08 324/303 |
| 2008/0221441 A1 * | 9/2008 | Bjornerud | ............. | G06T 7/0012 600/425 |

(Continued)

OTHER PUBLICATIONS

R. N. Sener, Diffusion MRI: apparent diffusion coefficient values in the normal brain and a classification of brain disorders based on ADC values, Computerized Medical Imaging and Graphics 25, 2001, 299-326.*

(Continued)

*Primary Examiner* — Sanjay Cattungal
(74) *Attorney, Agent, or Firm* — Quarles & Brady LLP (57) ABSTRACT

Methods for quickly estimating apparent diffusion coefficient probability density functions (ADC PDFs) for each image voxel are provided using a "diffusion reproducibility evaluation and measurement" (DREAM) magnetic resonance sequence. Non-diffusion-weighted (reference) images collected simultaneously have blood oxygenation level dependent (BOLD) sensitivity that can be used for resting-state fMRI data to measure functional connectivity, an unbiased parameter reflecting neurological integrity. ADC coefficient of variation (ADC CV) measurements can be used to isolate and label regions of non-enhancing tumor and predict future enhancement independent of FLAIR, T2, or average ADC maps. Functional diffusion mapping (fDMs) using voxel-wise changes in ADC PDFs can be used to spatially visualize and statistically quantify response to treatment. Additionally, the temporal (time-resolved) diffusivity information can be used for real-time MR thermometry, which is useful for cancer treatment monitoring, and for microperfusion quantification, and tumor/tissue characterization.

14 Claims, 6 Drawing Sheets

(51) Int. Cl.
*G01R 33/563* (2006.01)
*G01R 33/565* (2006.01)
*G01R 33/561* (2006.01)

(58) Field of Classification Search
USPC .................................................. 600/407–430
See application file for complete search history.

(56) References Cited

U.S. PATENT DOCUMENTS

| | | | | |
|---|---|---|---|---|
| 2009/0035218 | A1* | 2/2009 | Ross | A61B 5/415 424/9.1 |
| 2012/0112743 | A1* | 5/2012 | Granlund | G01R 33/5614 324/309 |
| 2013/0329973 | A1* | 12/2013 | Cao | A61B 5/0033 382/128 |
| 2015/0374721 | A1* | 12/2015 | Njar | A61K 31/58 514/176 |
| 2016/0018501 | A1* | 1/2016 | Kimura | A61B 5/055 324/322 |
| 2016/0157746 | A1* | 6/2016 | Ellingson | A61B 5/055 600/420 |
| 2017/0216624 | A1* | 8/2017 | Kondziolka | A61B 6/507 |
| 2017/0261584 | A1* | 9/2017 | James | A61B 5/055 |
| 2017/0301086 | A1* | 10/2017 | Jena | A61B 5/055 |

OTHER PUBLICATIONS

Barajas et al., Glioblastoma Multiforme Regional Genetic and Cellular Expression Patterns: Influence on Anatomic and Physiologic MR Imaging, Radiology, 2010; 254(2): 564-576.

Ellingson et al., Validation of Functional Diffusion Maps (fDMs) as a Biomarker for Human Glioma Cellularity. J Magn Reson Imaging, 2010; 31(3): 538-548.

Sugahara et al., Usefulness of diffusion-weighted MRI with echo-planar technique in the evaluation of cellularity in gliomas, J Magn Reson Imaging, 1999; 9:53-60.

Lu et al, Diffusion-Tensor MR Imaging of Intracranial Neoplasia and Associated Peritumoral Edema: Introduction of the Tumor Infiltration Index, Radiology, 2004; 232(1): 221-8.

Gerstner et al., Infiltrative Patterns of Glioblastoma Spread Detected via Diffusion MRI After Treatment with Cediranib, Neuro-Oncology, 2010; 12(5): 466-472.

Pavlisa et al., The Differences of Water Diffusion Between Brain Tissue Infiltrated by Tumor and Peritumoral Vasogenic Edema, Clin Imaging, 2009; 33(2): 96-101.

McMillan et al., Physiologic Characterisation of Glioblastoma Multiforme Using MRI-Based Hypoxia Mapping, Chemical Shift Imaging, Perfusion and Diffusion maps, J Clin Neurosci, 2006; 13(8): 811-7.

Chenevert et al., Diffusion Magnetic Resonance Imaging: an Early Surrogate Marker of Therapeutic Efficacy in Brain Tumors, JNCI: Journal of the National Cancer Institute, 2000; 92(24): 2029-2036.

Jakab et al., Glioma Grade Assessment by Using Histogram Analysis of Diffusion Tensor Imaging-Derived Maps, Neuroradiology, 2011; 53(7): 483-491.

Pope et al., Recurrent Glioblastoma Multiforme: ADC Histogram Analysis Predicts Response to Bevacizurnab Treatment, Radiology, 2009; 252(1): 182-189.

Khayal et al., Evaluation of Diffusion Parameters as Early Biomarkers of Disease Progression in Glioblastoma Multiforme, Neuro-Oncology, 2010; 12(9): 908-916.

Ellingson et al., Volumetric Analysis of Functional Diffusion Maps is a Predictive Imaging Biomarker for Cytotoxic and Anti-Angiogenic Treatments in Malignant Gliomas. J Neurooncol. 2010; 102(1): 95-103.

Sasaki et al., Variability in Absolute Apparent Diffusion Coefficient Values across Different Platforms May Be Substantial: A Multivendor, Multi-institutional Comparison Study, Radiology, 2008; 249(2): 624-630.

Cohen et al., The Effects of Perfusion on Diffusion Changes in Human Brain Tumors, J Magn Reson Imaging, 2013; 38(4): 868-875.

Le Bihan et al., Separation of Diffusion and Perfusion in Intravoxel Incoherent Motion MR Imaging, Radiology, 1988; 168(2): 497-505.

Holodny et al., Correlation Between the Degree of Contrast Enhancement and the Volume of Peritumoral Edema in Meningiomas and Malignant Gliomas, Neuroradiology, 1999; 41(11): 820-5.

Sener, R. N. "Diffusion MRI: apparent diffusion coefficient (ADC) values in the normal brain and a classification of brain disorders based on ADC values." Computerized medical imaging and graphics 25.4 (2001): 299-326.

* cited by examiner

DIFFUSION REPRODUCIBILITY EVALUATION AND MEASUREMENT (DREAM)-MRI IMAGING METHODS

CROSS-REFERENCE TO RELATED APPLICATIONS

This application claims priority to, and the benefit of, U.S. provisional patent application Ser. No. 62/085,715 filed on Dec. 1, 2014, incorporated herein by reference in its entirety.

STATEMENT REGARDING FEDERALLY SPONSORED RESEARCH OR DEVELOPMENT

This invention was made with Government support under CA167354, awarded by the National Institutes of Health. The Government has certain rights in the invention.

INCORPORATION-BY-REFERENCE OF COMPUTER PROGRAM APPENDIX

Not Applicable

BACKGROUND

1. Technical Field

The present technology pertains generally to magnetic resonance diagnostic imaging methods and more particularly to methods that simultaneously acquire estimates of the ADC probability density function (ADC PDF) as well as estimate functional connectivity in patients with primary brain tumors using a sequence termed diffusion repeatability evaluation and measurement (DREAM)-MRI, that allows an estimation of uncertainty in ADC quantification by approximating the voxel-wise ADC probability density function (PDF) distribution.

2. Background

Diffusion MRI is an important, yet controversial quantitative cancer imaging biomarker. Diffusion-weighted MRI (or DWI) is a technique that typically attempts to elicit subvoxel information about brain tumor microstructural features. DWI measures of apparent diffusion coefficient (ADC) have been shown to be sensitive to brain tumor cellularity, tumor invasion, the presence of cerebral edema, tissue hypoxia, and the response to therapy. Diffusion characteristics have also been shown to correlate with histopathological grading of gliomas and can be an important predictive and prognostic biomarker for a variety of brain tumor therapies.

The apparent diffusion coefficient (ADC), or magnitude of random water movement within tumors, can be used to estimate tumor cell density, allowing clinicians to monitor and predict treatment response. However, ADC maps/images that are acquired clinically are only an estimate of ADC within the tissue, and therefore are prone to measurement inaccuracies and physiologic noise.

Traditional ADC maps that use a single measurement of apparent diffusion coefficients (ADC) using diffusion MRI do not allow for an estimation of variability in the ADC measurements and may fail to capture the complexity of the tumor microstructure. Clinical MR measures of ADC typically involve a single measurement in three orthogonal directions, then the calculation of the average "isotropic", or "trace" ADC using information about the level of diffusion weighting (i.e. b-value). Thus, the resulting ADC maps acquired clinically in the art can be considered a single estimate of mean tissue ADC within a voxel. Studies have shown that normal tissue can have variability in ADC estimation of ADC as high as 30% and data from multicenter clinical trials suggest estimation of mean ADC can vary significantly across scanners, field strengths, and acquisition protocols.

Since ADC measurements within brain tumors vary over time and follow highly complex PDF distributions, single estimates of ADC using traditional diffusion MR approaches are often inadequate for characterizing brain tumor tissues. Despite the promising potential, the many sources of variability in ADC measurements exist, resulting in skepticism about the potential widespread applicability of ADC as a reliable and robust imaging biomarker for use in cancer clinical trials.

Accordingly, there is a need for new diffusion MR methods that allows for estimation of uncertainty in ADC quantification by approximating the voxel-wise ADC PDF distribution.

BRIEF SUMMARY

Diffusion MRI is widely recognized as an important cancer imaging biomarker for characterizing brain tumor cellularity, estimating aggressivity, and predicting patient response to therapy. However, traditional diffusion MR techniques do not take into consideration variability in ADC measurement and often fails to capture the complexity of the tumor microstructure.

The present technology introduces a new approach to diffusion MR quantification termed diffusion repeatability evaluation and measurement (DREAM)-MRI that allows an estimation of uncertainty in ADC quantification by approximating the voxel-wise ADC probability density function (PDF) distribution. The technique allows for the estimation of uncertainty in diffusion characteristics along with other added benefits (fMRI, BOLD sensitivity, fDWI, etc).

The DREAM-MRI imaging method is a simple way of estimating the ADC PDF within clinically realizable scanning times. Results suggest that the DREAM-MRI quantification of ADC PDFs may be a particularly sensitive method for quantifying tumor behavior and identifying tumor progression, thereby improving patient care by providing clinicians with a better tool for assessing patient response. Although applied to brain tumors, similar techniques can be applied to other cancer types and tissue types.

The imaging technique involves the rapid acquisition of hundreds of diffusion weighted images within a short scan time. Since the images are acquired so rapidly, the non-diffusion-weighted (reference) images have blood oxygenation level dependent (BOLD) sensitivity, allowing for simultaneous acquisition of fMRI information in one embodiment.

One advantage of the DREAM-MRI technique includes the generation of apparent diffusion coefficient probability density functions (ADC PDFs) along with the simultaneous quantification of fMRI information. The non-diffusion-weighted (reference) images collected simultaneously can be used as resting-state fMRI data to measure functional connectivity, an unbiased parameter thought to reflect neurological integrity. The temporal (time-resolved) diffusivity information can be used for real-time MR thermometry, which is useful for cancer treatment monitoring. Additionally, the time series diffusivity information may be useful for MR microperfusion quantification, etc. and the ADC PDF is useful for quantification and characterization of tumor/tissue heterogeneity, for example.

In one embodiment, the method comprises rapidly acquiring a number of diffusion weighted magnetic resonance images over a scan time; approximating apparent diffusion coefficient probability density function (ADC-PDF) distributions for voxels from the acquired diffusion weighted magnetic resonance images; and then mapping the probability density at each ADC value for each image voxel to produce a final ADC-PDF map or image. The ADC-PDF map is a parametric image of apparent diffusion coefficients probability density function values for each voxel.

In another embodiment, the method further includes collecting simultaneously non-diffusion weighted magnetic resonance images and then measuring the functional connectivity with resting-state fMRI data from the collected images.

In another embodiment, the method for tumor imaging in tissue comprised acquiring a number of diffusion weighted magnetic resonance images of at least two b-values over a short scan time; calculating apparent diffusion coefficient values for said b-values from the acquired images; approximating apparent diffusion coefficient probability density function (ADC-PDF) distributions for each voxel; mapping (ADC-PDF) distributions of the probability density at each ADC value for each image voxel to produce an image; and then identifying areas of comparatively lower ADC values within tissue regions of interest from the map/image.

In one preferred embodiment, the diffusion weighted magnetic resonance images are acquired with a single-shot echo polar (SS-EPI) sequence with parallel imaging and partial Fourier encoding. The speed of image acquisition can be increased with the use of a spiral pulse sequence or with compressed sensing techniques.

The DREAM-MRI sequence and methods were applied to variety of phantoms, healthy control participants, and patients with primary gliomas to demonstrate the technology. The phantom studies suggested an optimal b-value of 500 s/mm$^2$ for minimal variance in ADC. ADC variability was observed to change linearly with choice of repetition time, but not number of acquisitions, direction, or tissue T1. Test-retest reliability demonstrated good concordance between serial measurements in both phantoms and healthy tissues.

Complex ADC PDF characteristics were observed in biologically heterogeneous tumors, suggesting ADC PDFs may be a good new method of quantifying tumor heterogeneity. These complex ADC PDFs were independent of tissue perfusion and diffusion direction, but occurred most frequently in metabolically active tumor as measured using $^{18}$F-FDG PET. ADC coefficient of variation (ADC CV) measurements of less than 5% appeared to isolate and label regions of non-enhancing tumor and predict future enhancement independent of FLAIR, T2, or average ADC maps.

Functional diffusion mapping (fDMs) using voxel-wise changes in ADC PDFs could be used to spatially visualize and statistically quantify treatment response. Resting-state fMRI networks extracted from DREAM-MRI data in volunteers and patients were anatomically consistent with known functional networks, including in the default mode network.

According to one aspect of the technology, a DREAM-MRI imaging method is provided that allows for quantification of voxel-wise ADC probability density functions (PDFs), allowing assessment of variability and confidence in ADC measurements.

According to another aspect of the technology, DREAM-MRI sequence and method is provided for simultaneously characterizing brain tumor microstructure and neurological integrity by estimating the voxel-wise ADC PDF, exploring new image contrasts including ADC CV, statistically comparing diffusion measurements over time, and simultaneously estimating functional connectivity from resting-state fMRI signals.

Another aspect of the technology is to provide a new technique that allows for estimation of uncertainty in diffusion characteristics along with other added benefits (fMRI, BOLD sensitivity, fDWI, etc).

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawing which is for illustrative purposes only.

DETAILED DESCRIPTION

Referring more specifically to the drawings, for illustrative purposes, embodiments of the apparatus and methods for controlling the magnetostrictive anisotropy of magnetic units with patterned electrodes creating localized biaxial strain in a piezoelectric substrate are generally shown. Several embodiments of the technology are described generally in FIG. 1 through FIG. 4C to illustrate the diagnostic sequence and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
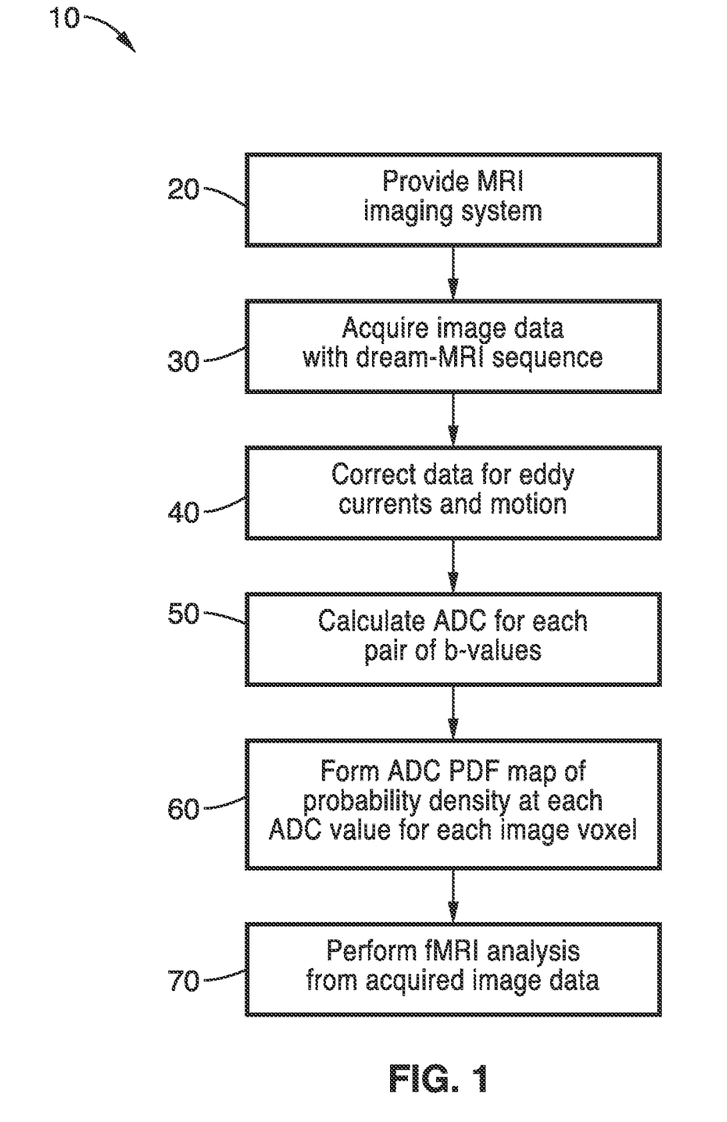
FIG. 1 is a schematic flow diagram of one method of estimating the apparent diffusion coefficient (ADC) probability density function (PDF) using diffusion repeatability evaluation and measurement (DREAM)-MRI.

Turning now to FIG. 1, one method 10 for tissue imaging is generally shown. The method preferably uses hundreds of diffusion weighted images within a short scan time using a diffusion repeatability evaluation and measurement (DREAM)-MRI sequence to estimate the apparent diffusion coefficient (ADC) probability density function (PDF) for each voxel. The DREAM-MRI method is a valuable method for simultaneously characterizing brain tumor microstructure and neurological integrity by estimating the voxel-wise ADC PDF, exploring new image contrasts including ADC CV, statistically comparing diffusion measurements over time, and simultaneously estimating functional connectivity from resting-state fMRI signals.

At block 20 of FIG. 1, a standard magnetic resonance imaging system can be used to acquire image data from a subject. Diffusion-weighted magnetic resonance (MR) imaging (DWI) is a well known tool for detecting abnormal water diffusion in the brain, for example. MRI dealing with microscopic motion within a single voxel is referred to as diffusion weighted imaging.

The typical MRI system at block 20 includes a MR scanner with a workstation that includes a display, keyboard and a programmable computer processor configured to run software programming. The workstation provides an operator interface and control over the components of the MRI system through software instructions and operator input. The workstation also records acquired data from the MRI system.

Image data from the MRI system is acquired at block 30 of FIG. 1 preferably with the use of the DREAM-MRI sequence used a single-shot echo planar (SS-EPI) acquisition technique. DREAM-MRI data is obtained by rapidly acquiring b=0 and b>0 s/mm$^2$ diffusion-weighted images hundreds of times over a single scan session. The flip angle, echo time (TE), repetition time (TR), etc. can be adjusted for varying BOLD sensitivity. In one preferred embodiment, the diffusion weighted magnetic resonance images are acquired with a single-shot echo polar (SS-EPI) sequence with parallel imaging and partial Fourier encoding. The speed of image acquisition can also be increased with the use of a spiral pulse sequence or with compressed sensing techniques. Although this sequence is preferred, other DWI sequences and techniques can be used.

At block 40 of FIG. 1, the data set of acquired diffusion weighted magnetic resonance images of at least two b-values over a short scan time at block 30 is optionally corrected for motion artifacts and distortions. For example, the DREAM-MRI data at 2 b-values can be eddy current and motion corrected using FSL of SPM software. For example, a single volume (b-value=0) can be acquired and used as a reference to correct for eddy currents and head motion.

At block 50 of FIG. 1, ADC maps for each pair of b-values ($b_1$ and $b_2$) that are used are then calculated using the formula: $ADC=-1/(b_2-b_1)\times \ln(Sb_2/Sb_1)$. Voxel-wise ADC values collected over the entire scan time can be collapsed into a histogram and then divided by the total number of acquisitions, resulting in the final ADC PDF map reflecting the probability density at each ADC value for each image voxel. The calculated ADC for each pair of b=0 and b>0 s/mm$^2$ images results in an ADC time series dataset reflecting ADC values in each voxel over the entire scan session at block 60 of FIG. 1.

At block 70 of FIG. 1, the acquired data is used for fMRI analysis. Acquisition of b=0 s/mm$^2$ images over time have BOLD sensitivity and can be used for fMRI analysis using standard techniques. For example, if no functional paradigm is used, the fMRI data can be used for resting-state fMRI analysis using independent component analysis.

The acquired data at block 60 and block 70 can also be used to make other evaluations. For example, comparing ADC-PDF maps from serial scans can be used to identify decreases in ADC in voxels of contrast enhancing regions of the maps as an indicator of tumor recurrence. Coefficient of variation (ADC CV) measurements for a region of interest of a subject tissue can also be collected and regions of non-enhancing tumor can be labeled and future contrast enhancements of areas of tissue can be predicted. Additionally, the time series diffusivity information may be useful for MR thermometry, microperfusion quantification, and tumor/tissue characterization.

The technology described herein may be better understood with reference to the accompanying examples, which are intended for purposes of illustration only and should not be construed as in any sense limiting the scope of the technology described herein as defined in the claims appended hereto.

Example 1

Although diffusion MRI is an important cancer imaging biomarker, traditional diffusion MR techniques do not consider the variabilities in ADC measurements. ADC measurements within brain tumors vary over time and follow highly complex PDF distributions, suggesting single estimates of ADC using traditional diffusion MR approaches may not be adequate for characterizing brain tumor tissues.

The methods of the present technology overcome these issues with a new approach to diffusion MR quantification termed diffusion repeatability evaluation and measurement (DREAM)-MRI that allows for estimation of uncertainty in ADC quantification by approximating the voxel-wise ADC probability density function (PDF) distribution. The DREAM-MRI sequence is used to measure the voxel-wise ADC PDFs in water phantoms, healthy volunteers, and patients with brain tumors in Examples 2-4 respectively.

To demonstrate the Diffusion Reproducibility Evaluation and Measurement (DREAM)-MRI methods, the DREAM-MRI sequence was implemented on a 3T MR system (Siemens Trio Tim; Siemens Medical, Erlangen, Germany) using standard clinical gradients and an 8-channel head coil. For all experiments, including the subsequent examples, the DREAM-MRI sequence used a single-shot echo planar (SS-EPI) acquisition technique, an acquisition matrix of 128×128, flip angle of 90 degrees, TE=85-120 ms, ⅝ partial Fourier encoding, and parallel imaging (GRAPPA=2) for a total of 10 slices with 5 mm slice thickness and no interslice gap. These parameters allowed for a TR as short as 1.2 seconds, or estimation of ADC along a single direction in as short as 2.4 seconds using 2 b-values, while maintaining adequate coverage for most tumor patients (~5 cm in the z-direction). The flip angle, TE, TR, etc. can be adjusted to vary BOLD sensitivity.

The apparent diffusion coefficient probability density function (ADC PDF) was estimated by obtaining hundreds to thousands of ADC maps during a short period of time. After acquisition of DREAM-MRI data at 2 b-values, data was eddy current and motion corrected using FSL. ADC maps for each pair of b-values ($b_1$ and $b_2$) that were used were then calculated as $ADC=-1/(b_2-b_1)\times \ln(S_{b2}/S_{b1})$.

Voxel-wise ADC values collected over the entire scan time were collapsed into a histogram and then divided by the total number of acquisitions resulting in the final ADC PDF map reflecting the probability density at each ADC value for each image voxel.

FMRI Calculations can also be made. Acquisition of b=0 s/mm² images over time have BOLD sensitivity and can be used for fMRI analysis using standard techniques. If no functional paradigm is used, the fMRI data can be used for resting-state fMRI analysis (using independent component analysis, for example).

It will be appreciated that the technology described herein is an MRI technique that would be employed on an MRI system. This technique may replace 2-3 different MR sequences and provide novel information about malignant cancerous tissues and normal tissues.

Example 2

In order to further demonstrate the technology, DREAM-MRI acquisition parameters were optimized using water phantoms by minimizing ADC variability. A total of four different experiments were performed using either the American College of Radiology (ACR) water phantom (Model: J10371) or the Magphan® EMR051 Alzheimer's disease neuroimaging initiative (ADNI) phantom aimed at exploring the influence of DREAM-MR scan parameters on measurements of ADC variability. Phantom experiments for optimization of DREAM-MRI acquisition parameters are shown in FIG. 2A through FIG. 2D.

Experiment 1 consisted of an examination of the effects of b-value by averaging voxel-wise ADC variability within the isotropic area of the ACR phantom (i.e. center slices with no structures) using a single b=0 s/mm² image and b-values from 50 to 1400 s/mm² and TE/TR=115 ms/1500 ms.

Figure 2A:
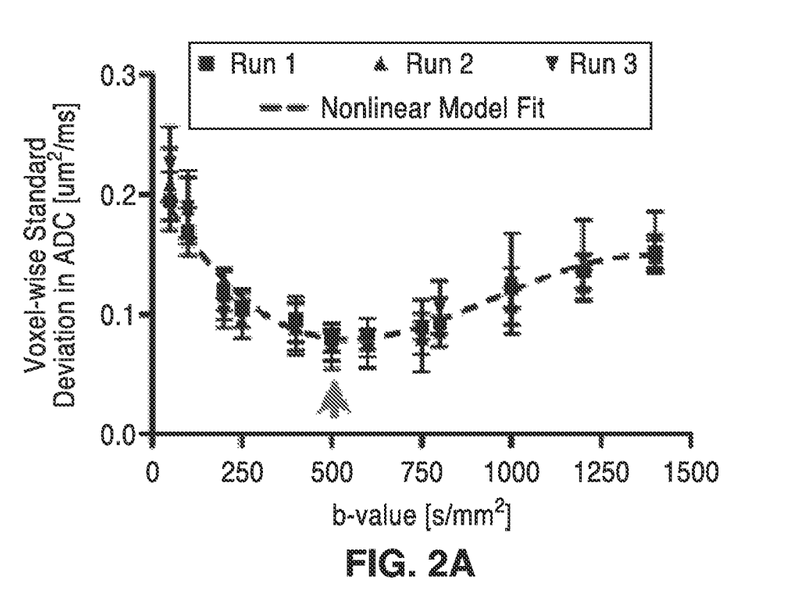
FIG. 2A is a graph of a comparison of voxel-wise ADC variability measurements across a range of b-values from 50 to 1400 s/mm$^2$. Results suggest an optimal b-value of 545.7 s/mm$^2$ to minimize ADC variability by using a third-order polynomial model to describe the relationship between ADC variability and b-value.

In order to assess the effects of b-value on ADC variability, the DREAM-MRI sequence was performed three times at a variety of b-values ranging from 50 to 1400 s/mm². FIG. 2A shows a comparison of voxel-wise ADC variability measurements across a range of b-values from 50 to 1400 s/mm². Results from the three different runs were in agreement, suggesting ADC standard deviation changed nonlinearly as a function of b-value as shown in FIG. 2A.

A third order polynomial was used to estimate this nonlinear relationship with the optimal equation:

$$\sigma(ADC) = 0.235 - b \cdot 0.696 \times 10^{-3} + b^2 \cdot 8.98 \times 10^{-7} - b^3 \cdot 3.18 \times 10^{-10}$$

(Nonlinear regression least squares, $P<0.0001$) over this range of b-values. Results suggested an optimal b-value of approximately 545.7 s/mm² (95% confidence interval 490.6-600.8 s/mm²) for minimal variability in ADC.

Figure 2B:
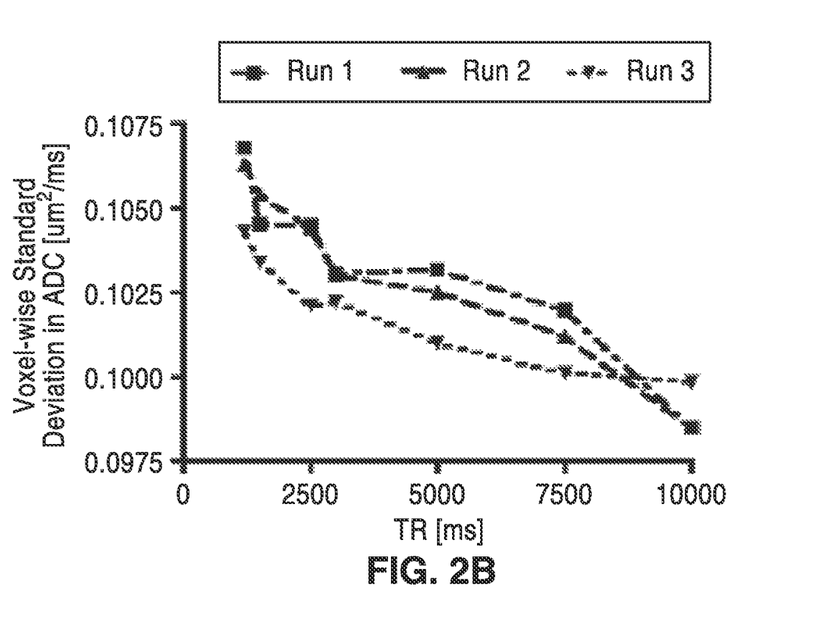
FIG. 2B is a graph of a comparison of voxel-wise ADC variability measurements across repetition times (TRs). Results suggest a linear trend between ADC variability and TR.

Experiment 2 examined the effects of TR on ADC variability by keeping the b-value constant at 0 and 500 s/mm² and then varying TR from 1200 to 10000 ms. Using a b-value of 500 s/mm², ADC variability was found to be inversely proportional to TR as shown in FIG. 2B (Pearson's Correlation Coefficient, $R^2=0.80$, $P<0.0001$). However, the magnitude of change in ADC variability over the range of TR values was relatively small, varying less than 1% over the range of TR values tested when compared to average ADC measurements.

Experiment 3 examined the effects of tissue T1 on measurements of ADC variability by using the Magphan® EMR051 ADNI phantom, which houses containers with target T1 values of 450 ms, 600 ms, 750 ms, and 900 ms at 3T. ADC estimates were obtained using b=0 and 500 s/mm² images and a TE/TR=100 ms/1500 ms. For Experiments 1-3, a total of 150 ADC maps were acquired over 8 minutes (50 samples in the x, y, and z directions).

Figure 2C:
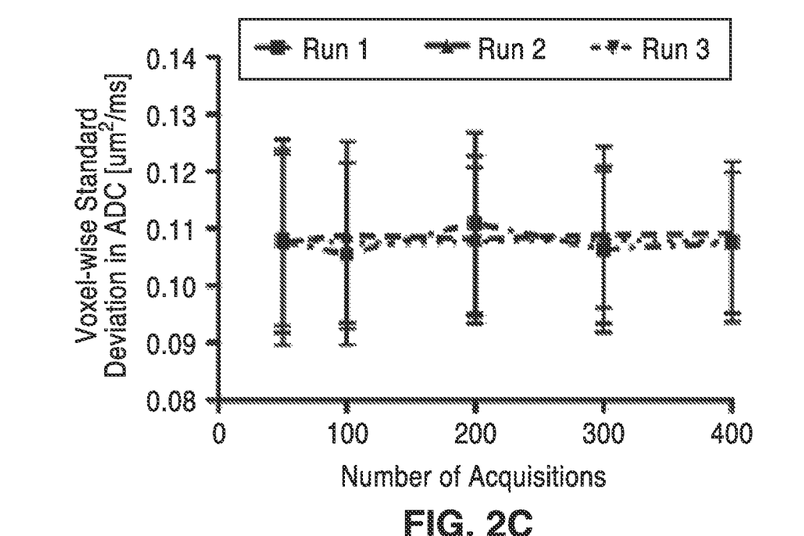
FIG. 2C is a graph of a comparison between voxel-wise ADC variability for various numbers of acquisitions (NEX).
Figure 2D:
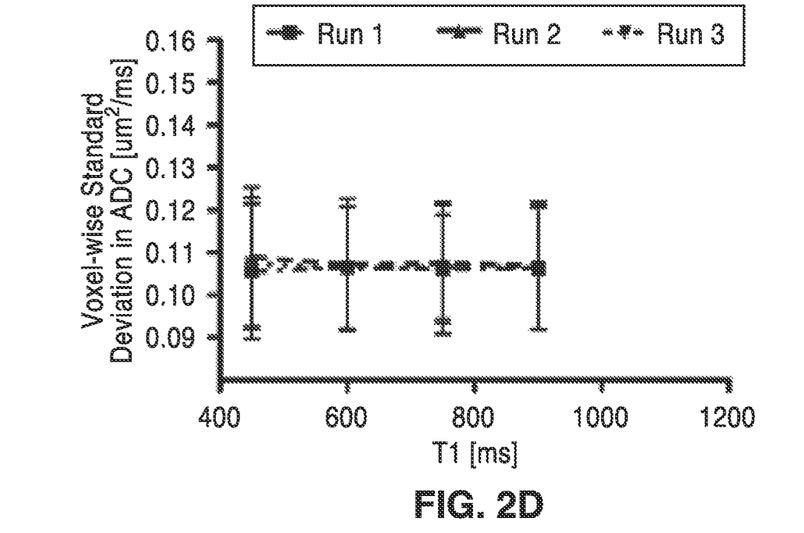
FIG. 2D is a graph of a comparison between voxel-wise ADC variability and tissue T1 as measured using the ADNI phantom.

Lastly, Experiment 4 examined the effect of the total number of acquisitions on ADC variability by varying the number of acquisitions from 50 to 400 using b=0/500 s/mm² and TE/TR=85 ms/1500 ms. All of the experiments were repeated immediately after the first acquisition (test-retest, Run 2), as well as two weeks later (Run 3). The results suggested that ADC variability was not dependent on the number of acquisitions as seen in FIG. 2C (Repeated-Measures ANOVA, P=0.6918) or tissue T1 as seen in FIG. 2D (Repeated-Measures ANOVA, P=0.4952). Based on these results, a b-value of 500 s/mm² and TR value of 1.5 seconds were used for subsequent experiments.

Example 3

The ADC PDF characteristics for neurologically-intact healthy volunteers (n=20) were evaluated using both standard clinical MRI and DREAM-MRI acquisitions. Regions of interest for normal-appearing white matter (NAWM), normal-appearing deep gray matter ($NAGM_{Deep}$), cerebrospinal fluid (CSF), and normal-appearing cortical gray matter (NAGM) were observed.

A total of 20 neurologically-intact, healthy volunteers (ages 22-35, 16 males, 4 females) were enrolled and gave their informed written consent to participate. Initially, anatomical and diffusion MRI scans were obtained in all patients using standard clinical protocols. Patients received an axial T2-weighted fast spin-echo, axial fluid-attenuated inversion recovery (FLAIR) sequence, and pre-contrast T1-weighted images. In addition to DREAM-MRI, an isotropic (3-direction) clinical DWI scan was obtained with b=0, 500, and 1000 s/mm². Lastly, contrast-enhanced T1-weighted images (T1+C) were obtained after injection of 0.1 mmol/kg gadopentetate dimeglumine (Gd-DTPA; Magnevist®, Bayer Scering Pharma AG, Leverkusen, Germany) contrast using the same pulse sequence parameters as used with the pre-contrast T1-weighted images.

DREAM-MRI acquisitions were then performed using a SS-EPI sequence with ⅝ partial Fourier and parallel imaging, 10 slices with slice thickness of 5 mm (no gap), TE/TR=85 ms/1500 ms, and b=0/500 s/mm². A total of 150 estimates of ADC were obtained over 8 minutes (50 in the x, y, and z orientation). Population-based composite ADC PDFs were created for cerebrospinal fluid (CSF), normal appearing white matter (NAWM), normal appearing cortical gray matter (NAGM), and normal appearing deep gray matter ($NAGM_{deep}$). A subset of 10 volunteers were scanned twice, their images registered, and then a voxel-wise comparison of ADC PDFs was performed.

Figure 3:
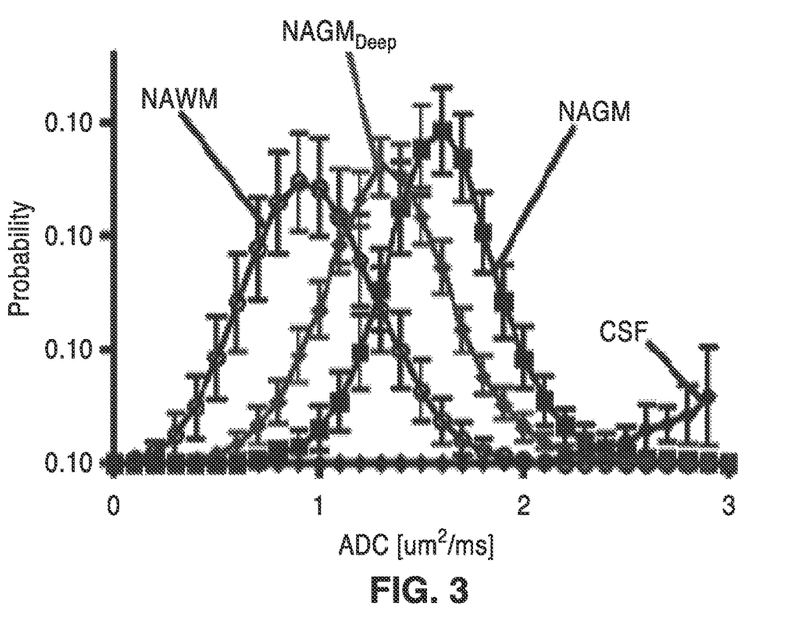
FIG. 3 is a graph of ADC PDFs averaged across all healthy volunteers for regions of interest for normal-appearing white matter (NAWM), normal-appearing deep gray matter (NAGM$_{Deep}$), cerebrospinal fluid (CSF), and normal-appearing cortical gray matter (NAGM).

Results from the examination of ADC PDF characteristics in regions of NAWM, NAGM, and $NAGM_{Deep}$ within 20 healthy volunteers verified the stability and repeatability of these measurements. As seen in FIG. 3, the ADC PDF distributions from NAWM, NAGM, and $NAGM_{Deep}$ across all 20 volunteers appeared to be normally distributed with an average ADC value of approximately 0.95 um²/ms (Nonlinear regression, Gaussian Distribution, $R^2=0.3733$), 1.59 um²/ms (Nonlinear regression, Gaussian Distribution, $R^2=0.4974$), and 1.33 um²/ms (Nonlinear regression, Gaussian Distribution, $R^2=0.6389$), respectively.

A Test-retest reliability evaluation was then performed in a subset of 10 volunteers by co-registering ADC PDFs and performing a Kolmogorov-Smirnov test for each image voxel to determine which voxels contained statistically significant differences in the shape of the ADC PDF. Voxel-wise maps of Kolmogorov-Smirnov p-values showing repeatability of ADC PDF distributions within the brain using a 30 minute coffee-break experiment were created.

In general, ADC PDF distributions were not statistically different within central brain structures and representative examples of ADC PDFs within normal brain tissue showed good agreement between ADC PDF distributions. However, voxels near tissue boundaries (e.g. near the ventricles or edge of the brain) showed significant differences in ADC PDF distribution shapes, likely due to slight image misregistration and partial volume contamination.

Example 4

The technology was also demonstrated on brain tumor patients and the ADC PDFs acquired from brain tumor tissues. A total of 34 patients (median age=54) gave informed written consent to have their data collected and stored in a Neuro-Oncology database. A total of 25 patients were diagnosed with glioblastoma (9 newly diagnosed, post-surgical patients; 3 patients after their $1^{st}$ tumor recurrence; and 13 patients after 2 or more recurrences), 1 patient with an anaplastic astrocytoma, and 8 patients with low-grade gliomas (2 newly diagnosed, post-surgical patients, and 6 patients with >1 tumor recurrence). Five patients with glioblastoma had $^{18}$F-FDG PET image data available for comparison. Regions of contrast-enhancement and T2/FLAIR hyperintensity were segmented in AFNI for ADC PDF comparisons.

Intriguingly, highly complex ADC PDF characteristics within regions of suspected tumors in glioma patients were observed. The ADC PDF results within normal-appearing brain tissue tended to consist of a single distribution near values obtained in healthy volunteers as seen in the results of Example 3. Contrast-enhancing tumor tissue contralateral to this normal appearing tissue appeared to consist of bimodal ADC PDFs, suggesting these voxels may have a more complex microstructure compared to normal tissue. Similar trends could be seen in areas of non-enhancing or peritumoral edema within the same patient, which were also distinctly different from contralateral enhancing tissue.

In addition, a range of complexity was observed in the voxel-wise ADC PDF within both contrast-enhancing and T2/FLAIR abnormal tissues. In particular, approximately three distinct distributions of ADC PDFs within tumor regions that appeared in many patients, albeit to varying degrees. A low ADC PDF distribution with mean between 0.5-1.0 um$^2$/ms in almost all voxels with contrast-enhancement and many voxels containing T2/FLAIR signal abnormality. Additionally, a slightly higher ADC PDF distribution with mean between 1.0-2.0 um$^2$/ms was observed in many contrast-enhancing voxels, although the presence of this higher ADC PDF distribution was not observed in all voxels with T2/FLAIR abnormal signal intensity.

In addition to these two distinct ADC PDF distributions observed in many enhancing and non-enhancing tumor regions, an even higher ADC PDF distribution with mean between 2.0-3.0 um$^2$/ms was observed within heterogeneously enhancing or necrotic tumor regions. Results also confirmed that hypermetabolic tumor identified on $^{18}$F-FDG PET contained highly heterogeneous ADC PDFs, specifically containing at least two distinct ADC PDF distributions.

Figure 4A:
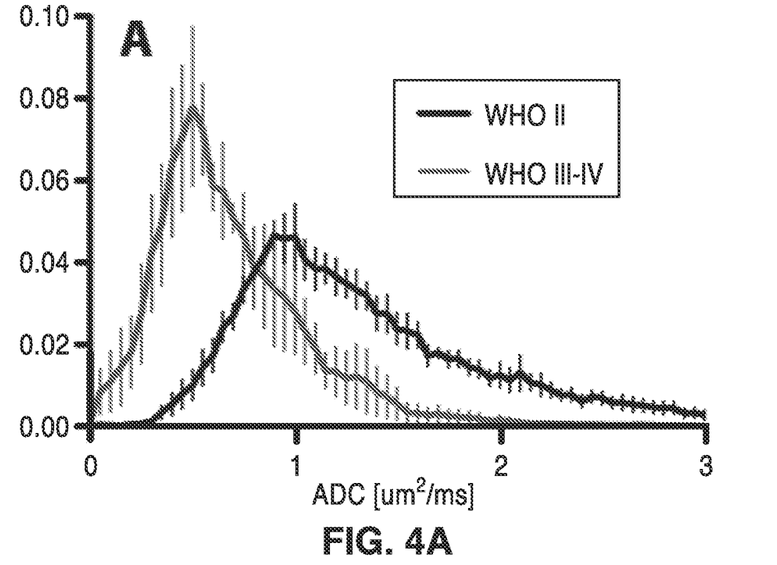
FIG. 4A is a graph of the average ADC PDF distributions within contrast-enhancing lesions in low-grade (WHO II, black lines) and high-grade (WHO III-IV, gray lines) gliomas.
Figure 4B:
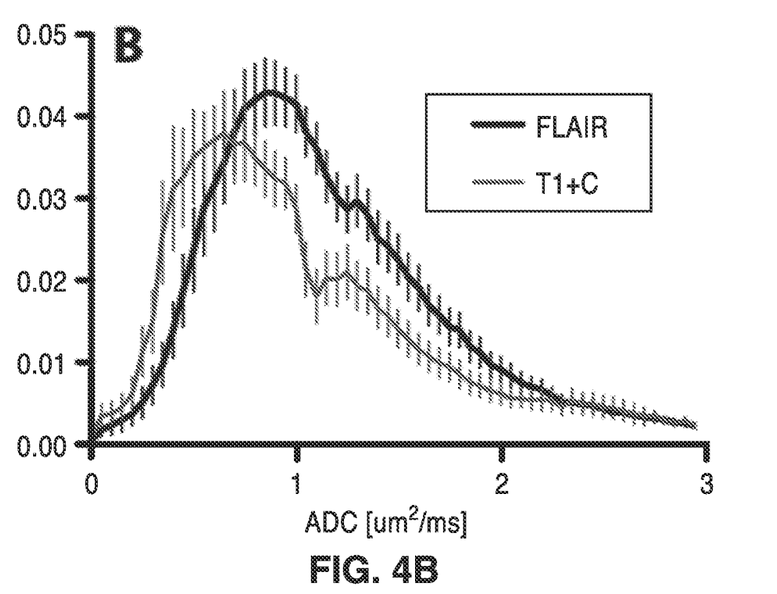
FIG. 4B is a graph of average ADC PDF distributions in T2/FLAIR hyperintense lesions (black lines) and contrast-enhancing lesions (T1+C, gray lines) in all glioma patients.
Figure 4C:
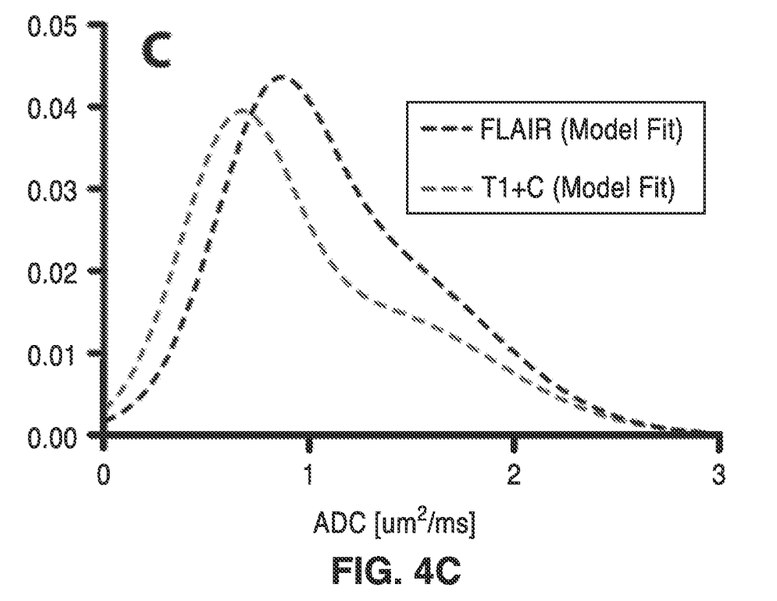
FIG. 4C is a graph of Double Gaussian mixed model fits for the average ADC PDF distributions shown in FIG. 4B.

Population-based average ADC PDF distributions in brain tumor patients are shown in FIG. 4A through FIG. 4C. Within contrast-enhancing tumors, substantially different distributions of ADC PDFs for low grade (WHO II) compared with malignant (WHO III-IV) gliomas were observed as shown in FIG. 4A. In particular, patients with malignant gliomas (WHO III-IV) tended to have lower average ADC PDFs compared to patients with low-grade (WHO II) gliomas.

Bimodal distributions in ADC PDFs were observed within T2/FLAIR hyperintense and contrast-enhancing ROIs when evaluated across all patients regardless of tumor grade as indicated in the graphs of FIG. 4B. In particular, a double Gaussian mixed model as shown in FIG. 4C was able to describe the average ADC PDFs within T2/FLAIR hyperintense as containing a low ADC distribution (ADC$_L$) with mean of 0.63±0.26 s.d. um$^2$/ms and a high ADC distribution (ADC$_H$) with mean 1.26±0.59 s.d. um$^2$/ms (Nonlinear regression, Double Gaussian Mixed Model, $R^2$=0.40). Within contrast-enhancing tumors, ADC$_L$ was found to be 0.82±0.28 s.d. um$^2$/ms and ADC$_H$ was found to be 1.36±0.55 s.d. um$^2$/ms (Nonlinear regression, Double Gaussian Mixed Model, $R^2$=0.47). ADC$_L$ values were determined to be statistically different between these two ROIs (F-test, P<0.0001); however, ADC$_H$ values were not different (F-test, P=0.4397), suggesting the distribution for ADC$_H$ may be similar between the two regions of interest.

Serial DREAM-MRI scans were also obtained in five glioblastoma patients during radiographic recurrence, resulting in a generalized shift in the ADC PDF distribution toward a lower ADC within image voxels containing new contrast-enhancement. This decrease in ADC is consistent with previous reports showing a decrease in ADC within contrast-enhancing regions at tumor recurrence. The differences in ADC PDF distributions in areas of new contrast enhancement during tumor progression observed in the five patients with glioblastoma demonstrated a trend toward lower ADC at the time of tumor recurrence. However, in some patients, a difference in ADC may not have been observed using standard techniques since skew of the ADC PDF distribution, not the mean, appeared different at the time of recurrence.

Surprisingly, the results indicated that there are regions of contrast enhancing, T2/FLAIR hyperintense, and hypermetabolic tumor present with complex, heterogeneous ADC PDFs that do not follow single Gaussian distributions. In particular, it has been observed that ADC PDFs within tumor tissue often manifest with one to three distributions of ADC values, consistent with a mixture of dense tumor (0.5 um$^2$/ms<ADC<1.0 um$^2$/ms), infiltrative or edematous tumor tissue (1.0 um$^2$/ms<ADC<2.0 um$^2$/ms), and/or highly diffuse or necrotic tissue (2.0 um$^2$/ms<ADC<3.0 um$^2$/ms).

Regardless of the underlying source of complexity observed in tumor ADC PDF distributions, the results have significant clinical implications, suggesting a single ADC measurement may grossly under-represent tumor behavior, since a single measurement can theoretically fall anywhere along the voxel-wise ADC PDF distribution. The large range along with non-Gaussian behavior of ADC PDF distributions observed in the current study may in part speak to large discrepancies in tumor ADC values reported across manufacturers and imaging sites.

There is an obvious dependence of ADC PDF distributions on tumor grade and tissue region of interest, with higher-grade and contrast-enhancing tumors presenting with an ADC PDF distribution skewed toward lower values of ADC compared with low-grade tumors or T2/FLAIR hyperintense lesions. This is consistent with reports showing a correlation between ADC and tumor grade and studies showing that contrast-enhancing tumor contains the most aggressive, dense portion of the tumor with lower ADC.

Additionally, a clear shift in voxel-wise ADC PDF distributions toward lower ADC values during tumor recurrence was observed, which is also consistent with the literature indicating an increase in cellularity at the time of tumor progression. Together, the results suggest voxel-wise ADC PDF distributions estimated from DREAM-MRI provide necessary information about the heterogeneity of the tumor environment and may allow for more accurate assessment of ADC characteristics within the tumor.

Accordingly, the DREAM-MRI method is a valuable technique for simultaneously characterizing brain tumor microstructure and neurological integrity by estimating the voxel-wise ADC PDF, exploring new image contrasts including ADC CV, statistically comparing diffusion measurements over time, and simultaneously estimating functional connectivity from resting-state fMRI signals.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the discussion above it will be appreciated that the technology described herein can be embodied in various ways, including the following:

1. A method for tissue evaluation, the method comprising: (a) rapidly acquiring a number of diffusion weighted magnetic resonance images over a scan time; (b) approximating apparent diffusion coefficient probability density function (ADC-PDF) distributions for voxels from the acquired diffusion weighted magnetic resonance images; and (c) mapping the probability density at each ADC value for each image voxel to generate and display a final ADC-PDF map.

2. The method of any preceding embodiment, further comprising: collecting ADC coefficient of variation (ADC CV) measurements for a region of interest of a subject tissue; labeling regions of non-enhancing tumor; and predicting future contrast enhancement of areas of tissue.

3. The method of any preceding embodiment, further comprising: comparing ADC-PDF maps from serial scans; and identifying decreases in ADC in voxels of contrast enhancing regions of the maps as an indicator of tumor recurrence.

4. The method of any preceding embodiment, wherein the diffusion weighted magnetic resonance images are acquired with a single-shot echo polar (SS-EPI) sequence with parallel imaging and partial Fourier encoding.

5. The method of any preceding embodiment, further comprising: increasing speed of image acquisition using a spiral pulse sequence.

6. The method of any preceding embodiment, further comprising: increasing speed of image acquisition with compressed sensing.

7. The method of any preceding embodiment, wherein the approximating apparent diffusion coefficient probability density function (ADC-PDF) distributions comprises: acquiring weighted magnetic resonance images data at 2 b-values; correcting data of eddy current and motion artifacts; calculating ADC for each pair of b-values (b1 and b2) that are acquired; collecting voxel-wise ADC calculated values over the entire scan time; and collapsing the ADC calculated values into a histogram and then dividing the values by the total number of acquisitions to produce a final ADC PDF map reflecting the probability density at each ADC value for each image voxel.

8. The method of any preceding embodiment, further comprising: collecting simultaneously non-diffusion weighted magnetic resonance images; and measuring functional connectivity with resting-state fMRI data using the collected images.

9. The method of any preceding embodiment, wherein the resting-state fMRI data is based on blood oxygen level-dependent (BOLD) contrast.

10. A method for tumor imaging in tissue, the method comprising: (a) acquiring a number of diffusion weighted magnetic resonance images of at least two b-values over a short scan time; (b) calculating apparent diffusion coefficient values for the b-values from the acquired images; (c) approximating apparent diffusion coefficient probability density function (ADC-PDF) distributions for each voxel; (d) mapping (ADC-PDF) distributions of the probability density at each ADC value for each image voxel to generate an (ADC-PDF) distribution map; and (e) identifying areas of comparatively lower ADC values within tissue regions of interest from the map.

11. The method of any preceding embodiment, further comprising: comparing ADC-PDF maps from serial scans; and identifying decreases in ADC in voxels of contrast enhancing regions of the maps as an indicator of tumor recurrence.

12. The method of any preceding embodiment, further comprising: collecting ADC coefficient of variation (ADC CV) measurements for a region of interest of a subject tissue; labeling regions of non-enhancing tumor; and predicting future contrast enhancement of areas of tissue.

13. The method of any preceding embodiment, further comprising: collecting simultaneously non-diffusion weighted magnetic resonance images; and measuring functional connectivity with resting-state fMRI data using the collected images.

14. The method of any preceding embodiment, wherein the resting-state fMRI data is based on blood oxygen level-dependent (BOLD) contrast.

15. The method of any preceding embodiment, wherein the diffusion weighted magnetic resonance images are acquired with a single-shot echo polar (SS-EPI) sequence with parallel imaging and partial Fourier encoding.

16. The method of any preceding embodiment, wherein the mapping apparent diffusion coefficient probability density function (ADC-PDF) distributions comprises: collecting voxel-wise ADC calculated b-values values over the entire scan time; and collapsing the ADC calculated values into a histogram and then dividing the values by the total number of acquisitions to produce a final ADC PDF map reflecting the probability density at each ADC value for each image voxel.

17. A method for tissue evaluation, the method comprising: (a) rapidly acquiring a number of diffusion weighted magnetic resonance images over a scan time; (b) rapidly acquiring a number of non-diffusion weighted magnetic resonance reference images over a scan time; (c) approximating apparent diffusion coefficient probability density function (ADC-PDF) distributions for voxels from the acquired diffusion weighted magnetic resonance images; (d) mapping the probability density at each ADC value for each image voxel to produce a final ADC-PDF map; and (e) measuring functional connectivity with resting-state fMRI data using the acquired images.

18. The method of any preceding embodiment, wherein the resting-state fMRI data is based on blood oxygen level-dependent (BOLD) contrast.

19. The method of any preceding embodiment, wherein the diffusion weighted magnetic resonance images are acquired with a single-shot echo polar (SS-EPI) sequence with parallel imaging and partial Fourier encoding.

20. The method of any preceding embodiment, further comprising: collecting ADC coefficient of variation (ADC CV) measurements for a region of interest of a subject tissue; labeling regions of non-enhancing tumor; and predicting future contrast enhancement of areas of tissue.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:
1. A method for tissue evaluation, the method comprising:
   (a) rapidly acquiring a number of diffusion weighted magnetic resonance images over a scan time using an acquisition able to time-resolve apparent diffusion coefficient (ADC) measurement variations;
   (b) approximating apparent diffusion coefficient probability density function (ADC-PDF) distributions for voxels from the acquired diffusion weighted magnetic resonance images;
   (c) mapping the probability density at each ADC value for each image voxel to generate and display a final ADC-PDF map;
   (d) collecting ADC coefficient of variation (ADC CV) measurements for a region of interest of a subject tissue;
   (e) labeling regions of non-enhancing tumor; and
   (f) predicting future contrast enhancement of areas of tissue.

2. A method for tissue evaluation, the method comprising:
   (a) rapidly acquiring a number of diffusion weighted magnetic resonance images over a scan time using an acquisition able to time-resolve apparent diffusion coefficient (ADC) measurement variations;
   (b) approximating apparent diffusion coefficient probability density function (ADC-PDF) distributions for voxels from the acquired diffusion weighted magnetic resonance images;
   (c) mapping the probability density at each ADC value for each image voxel to generate and display a final ADC-PDF map; and wherein the diffusion weighted magnetic resonance images are acquired with a single-shot echo polar (SS-EPI) sequence with parallel imaging and partial Fourier encoding.

3. The method of claim 2, further comprising:
increasing speed of image acquisition using a spiral pulse sequence.

4. The method of claim 2, further comprising:
increasing speed of image acquisition with compressed sensing.

5. A method for tissue evaluation, the method comprising:
(a) rapidly acquiring a number of diffusion weighted magnetic resonance images over a scan time using an acquisition able to time-resolve apparent diffusion coefficient (ADC) measurement variations;
(b) approximating apparent diffusion coefficient probability density function (ADC-PDF) distributions for voxels from the acquired diffusion weighted magnetic resonance images;
(c) mapping the probability density at each ADC value for each image voxel to generate and display a final ADC-PDF map;
wherein said approximating apparent diffusion coefficient probability density function (ADC-PDF) distributions comprises:
acquiring weighted magnetic resonance images data at 2 b-values;
correcting data of eddy current and motion artifacts;
calculating ADC for each pair of b-values ($b_1$ and $b_2$) that are acquired;
collecting voxel-wise ADC calculated values over the entire scan time; and
collapsing the ADC calculated values into a histogram and then dividing the values by the total number of acquisitions to produce a final ADC PDF map reflecting the probability density at each ADC value for each image voxel.

6. A method for tissue evaluation, the method comprising:
(a) rapidly acquiring a number of diffusion weighted magnetic resonance images over a scan time using an acquisition able to time-resolve apparent diffusion coefficient (ADC) measurement variations;
(b) approximating apparent diffusion coefficient probability density function (ADC-PDF) distributions for voxels from the acquired diffusion weighted magnetic resonance images;
(c) mapping the probability density at each ADC value for each image voxel to generate and display a final ADC-PDF map;
further comprising:
collecting simultaneously non-diffusion weighted magnetic resonance images; and
measuring functional connectivity with resting-state fMRI data using the collected images.

7. The method of claim 6, wherein said resting-state fMRI data is based on blood oxygen level-dependent (BOLD) contrast.

8. A method for tumor imaging in tissue, the method comprising:
(a) acquiring, with a repetition time (TR) of less than 2.4 seconds, a number of diffusion weighted magnetic resonance images of at least two b-values over a short scan time;
(b) calculating apparent diffusion coefficient values for said b-values from the acquired images;
(c) approximating apparent diffusion coefficient probability density function (ADC-PDF) distributions for each voxel;
(d) mapping (ADC-PDF) distributions of the probability density at each ADC value for each image voxel to generate a (ADC-PDF) distribution map; and
(e) identifying areas of comparatively lower ADC values within tissue regions of interest from the map.

9. The method of claim 8, further comprising:
comparing ADC-PDF maps from serial scans; and
identifying decreases in ADC in voxels of contrast enhancing regions of said maps as an indicator of tumor recurrence.

10. The method of claim 8, further comprising:
collecting ADC coefficient of variation (ADC CV) measurements for a region of interest of a subject tissue;
labeling regions of non-enhancing tumor; and
predicting future contrast enhancement of areas of tissue.

11. The method of claim 8, further comprising:
collecting simultaneously non-diffusion weighted magnetic resonance images; and
measuring functional connectivity with resting-state fMRI data using the collected images.

12. The method of claim 11, wherein said resting-state fMRI data is based on blood oxygen level-dependent (BOLD) contrast.

13. The method of claim 8, wherein said diffusion weighted magnetic resonance images are acquired with a single-shot echo polar (SS-EPI) sequence with parallel imaging and partial Fourier encoding.

14. The method of claim 8, wherein said mapping apparent diffusion coefficient probability density function (ADC-PDF) distributions comprises:
collecting voxel-wise ADC calculated b-values values over the entire scan time; and
collapsing the ADC calculated values into a histogram and then dividing the values by the total number of acquisitions to produce a final ADC PDF map reflecting the probability density at each ADC value for each image voxel.

* * * * *

UNITED STATES PATENT AND TRADEMARK OFFICE
CERTIFICATE OF CORRECTION

PATENT NO. : 10,524,686 B2
APPLICATION NO. : 14/956149
DATED : January 7, 2020
INVENTOR(S) : Benjamin M. Ellingson Page 1 of 1

It is certified that error appears in the above-identified patent and that said Letters Patent is hereby corrected as shown below:

In the Specification

Column 1, Please delete Lines 15, 16, and 17, and insert the following:
--This invention was made with government support under Grant No. CA167354, awarded by the National Institutes of Health. The government has certain rights in the invention.--

Signed and Sealed this
Twenty-fifth Day of February, 2020

Andrei Iancu
*Director of the United States Patent and Trademark Office*